(12) United States Patent
Bregulla

(10) Patent No.: US 8,920,488 B2
(45) Date of Patent: Dec. 30, 2014

(54) ENDOPROSTHESIS HAVING A STABLE ARCHITECTURE

(75) Inventor: Rainer Bregulla, Balingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 0 days.

(21) Appl. No.: 11/961,290

(22) Filed: Dec. 20, 2007

(65) Prior Publication Data
US 2009/0163996 A1 Jun. 25, 2009

(51) Int. Cl.
*A61F 2/06* (2013.01)
*A61F 2/91* (2013.01)
*A61F 2/915* (2013.01)

(52) U.S. Cl.
CPC .......... *A61F 2/91* (2013.01); *A61F 2002/91558* (2013.01); *A61F 2/915* (2013.01)
USPC ....................................................... 623/1.16

(58) Field of Classification Search
USPC ................................................. 623/1.15–1.2
See application file for complete search history.

(56) References Cited

U.S. PATENT DOCUMENTS

| | | |
|---|---|---|
| 4,475,972 A | 10/1984 | Wong |
| 4,580,568 A | 4/1986 | Gianturco |
| 4,738,740 A | 4/1988 | Pinchuk et al. |
| 4,743,252 A | 5/1988 | Martin, Jr. et al. |
| 4,759,757 A | 7/1988 | Pinchuk |
| 4,776,337 A | 10/1988 | Palmaz |
| 4,800,882 A | 1/1989 | Gianturco |
| 4,907,336 A | 3/1990 | Gianturco |
| 5,015,253 A | 5/1991 | MacGregor |
| 5,019,090 A | 5/1991 | Pinchuk |
| 5,041,126 A | 8/1991 | Gianturco |
| 5,059,211 A | 10/1991 | Stack et al. |
| 5,102,417 A | 4/1992 | Palmaz |
| 5,104,404 A | 4/1992 | Wolff |
| 5,116,360 A | 5/1992 | Pinchuk et al. |
| 5,122,154 A | 6/1992 | Rhodes |

(Continued)

FOREIGN PATENT DOCUMENTS

| | | |
|---|---|---|
| CA | 2309079 | 11/2004 |
| DE | 19840645 | 9/1998 |

(Continued)

OTHER PUBLICATIONS

U.S. Appl. No. 10/859,636, filed Mar. 30, 2011, Issue Notification.

(Continued)

*Primary Examiner* — Andrew Iwamaye
(74) *Attorney, Agent, or Firm* — Workman Nydegger; Jonathan D. Feuchtwang

(57) ABSTRACT

The present invention relates to an endoprosthesis having a web structure that is expandable from a contracted configuration to an expanded configuration and that includes a plurality of longitudinally adjacent web rings. Each of the web rings is defined by web elements disposed circumferentially around a longitudinal axis, which are adjoined one to the other at junction bends. A first junction bend in a first web ring is coupled to a second junction bend in a second web ring by a connector which includes three or more struts of essentially equal length that extend circumferentially in essentially parallel directions. The struts of the connector are adjoined in sequence by coupling segments that, in one embodiment of the invention, are arcuate in shape.

13 Claims, 6 Drawing Sheets

(56) References Cited

U.S. PATENT DOCUMENTS

| | | | |
|---|---|---|---|
| 5,133,732 | A | 7/1992 | Wiktor |
| 5,147,370 | A | 9/1992 | McNamara et al. |
| 5,163,951 | A | 11/1992 | Pinchuk et al. |
| 5,171,262 | A | 12/1992 | MacGregor |
| 5,221,261 | A | 6/1993 | Termin et al. |
| 5,282,823 | A | 2/1994 | Schwartz et al. |
| 5,292,331 | A | 3/1994 | Boneau |
| 5,314,444 | A | 5/1994 | Gianturco |
| 5,370,683 | A | 12/1994 | Fontaine |
| 5,378,239 | A | 1/1995 | Termin et al. |
| 5,380,299 | A | 1/1995 | Fearnot et al. |
| 5,421,955 | A | 6/1995 | Lau et al. |
| 5,443,458 | A | 8/1995 | Eury |
| 5,443,496 | A | 8/1995 | Schwartz et al. |
| 5,449,373 | A | 9/1995 | Pinchasik et al. |
| 5,449,382 | A | 9/1995 | Dayton |
| 5,476,508 | A | 12/1995 | Amstrup |
| 5,496,277 | A | 3/1996 | Termin et al. |
| 5,514,154 | A | 5/1996 | Lau et al. |
| 5,527,354 | A | 6/1996 | Fontaine et al. |
| 5,556,414 | A | 9/1996 | Turi |
| 5,569,295 | A | 10/1996 | Lam |
| 5,591,197 | A | 1/1997 | Orth et al. |
| 5,591,224 | A | 1/1997 | Schwartz et al. |
| 5,593,417 | A | 1/1997 | Rhodes |
| 5,593,442 | A | 1/1997 | Klein |
| 5,603,721 | A | 2/1997 | Lau et al. |
| 5,609,606 | A | 3/1997 | O'Boyle |
| 5,628,788 | A | 5/1997 | Pinchuk |
| 5,630,829 | A | 5/1997 | Lauterjung |
| 5,632,772 | A | 5/1997 | Alcime et al. |
| 5,639,278 | A | 6/1997 | Dereume et al. |
| 5,649,952 | A | 7/1997 | Lam |
| 5,651,174 | A | 7/1997 | Schwartz et al. |
| 5,653,747 | A | 8/1997 | Dereume |
| 5,670,161 | A | 9/1997 | Healy et al. |
| 5,674,242 | A | 10/1997 | Phan et al. |
| 5,674,277 | A | 10/1997 | Freitag |
| 5,693,085 | A | 12/1997 | Buirge et al. |
| 5,695,516 | A | 12/1997 | Fischell et al. |
| 5,697,971 | A | 12/1997 | Fischell et al. |
| 5,700,285 | A | 12/1997 | Myers et al. |
| 5,707,386 | A | 1/1998 | Schnepp-Pesch et al. |
| 5,707,388 | A | 1/1998 | Lauterjung |
| 5,709,703 | A | 1/1998 | Lukic et al. |
| 5,709,713 | A | 1/1998 | Evans et al. |
| 5,716,393 | A | 2/1998 | Lindenberg et al. |
| 5,723,003 | A | 3/1998 | Winston et al. |
| 5,723,004 | A | 3/1998 | Dereume et al. |
| 5,728,158 | A | 3/1998 | Lau et al. |
| 5,733,303 | A | 3/1998 | Israel et al. |
| 5,735,892 | A | 4/1998 | Myers et al. |
| 5,735,893 | A | 4/1998 | Lau et al. |
| 5,735,897 | A | 4/1998 | Buirge |
| 5,738,817 | A | 4/1998 | Danforth et al. |
| 5,741,325 | A | 4/1998 | Chaikof et al. |
| 5,741,327 | A | 4/1998 | Frantzen |
| 5,743,874 | A | 4/1998 | Fischell et al. |
| 5,749,880 | A | 5/1998 | Banas et al. |
| 5,755,771 | A | 5/1998 | Penn et al. |
| 5,755,772 | A | 5/1998 | Evans et al. |
| 5,755,774 | A | 5/1998 | Pinchuk |
| 5,755,781 | A | 5/1998 | Jayaraman |
| 5,769,884 | A | 6/1998 | Solovay |
| 5,776,161 | A | 7/1998 | Globerman |
| 5,776,181 | A | 7/1998 | Lee et al. |
| 5,776,183 | A | 7/1998 | Kanesaka et al. |
| 5,782,904 | A | 7/1998 | White et al. |
| 5,800,526 | A | 9/1998 | Anderson et al. |
| 5,807,404 | A | 9/1998 | Richter |
| 5,810,868 | A | 9/1998 | Lashinski et al. |
| 5,810,870 | A | 9/1998 | Myers et al. |
| 5,810,872 | A | 9/1998 | Kanesaka et al. |
| 5,814,063 | A | 9/1998 | Freitag |
| 5,817,126 | A | 10/1998 | Imran |
| 5,824,037 | A | 10/1998 | Fogarty et al. |
| 5,824,045 | A | 10/1998 | Alt |
| 5,824,048 | A | 10/1998 | Tuch |
| 5,824,054 | A | 10/1998 | Khosravi et al. |
| 5,824,059 | A | 10/1998 | Wijay |
| 5,827,321 | A | 10/1998 | Roubin et al. |
| 5,836,964 | A | 11/1998 | Richter et al. |
| 5,836,966 | A | 11/1998 | St. Germain |
| 5,843,120 | A | 12/1998 | Israel et al. |
| 5,843,158 | A | 12/1998 | Lenker et al. |
| 5,843,161 | A | 12/1998 | Solovay |
| 5,843,164 | A | 12/1998 | Frantzen et al. |
| 5,846,247 | A | 12/1998 | Unsworth et al. |
| 5,853,419 | A | 12/1998 | Imran |
| 5,855,598 | A | 1/1999 | Pinchuk |
| 5,855,600 | A | 1/1999 | Alt |
| 5,860,999 | A | 1/1999 | Schnepp-Pesch et al. |
| 5,861,027 | A | 1/1999 | Trapp |
| 5,868,781 | A | 2/1999 | Killion |
| 5,871,538 | A | 2/1999 | Dereume |
| 5,876,449 | A | 3/1999 | Starck et al. |
| 5,876,450 | A | 3/1999 | Johlin, Jr. |
| 5,895,406 | A | 4/1999 | Gray et al. |
| 5,897,589 | A | 4/1999 | Cottenceau et al. |
| 5,922,021 | A | 7/1999 | Jang |
| 5,928,248 | A | 7/1999 | Acker |
| 5,938,682 | A | 8/1999 | Hojeibane et al. |
| 5,948,018 | A | 9/1999 | Dereume et al. |
| 5,954,743 | A | 9/1999 | Jang |
| 5,968,091 | A | 10/1999 | Pinchuk et al. |
| 5,968,561 | A | 10/1999 | Batchelder et al. |
| 5,980,552 | A | 11/1999 | Pinchasik et al. |
| 5,984,965 | A | 11/1999 | Knapp et al. |
| 6,019,789 | A | 2/2000 | Dinh et al. |
| 6,027,526 | A | 2/2000 | Limon et al. |
| 6,033,433 | A | 3/2000 | Ehr et al. |
| 6,033,434 | A | 3/2000 | Borghi |
| 6,033,435 | A | 3/2000 | Penn et al. |
| 6,039,756 | A | 3/2000 | Jang |
| 6,048,361 | A | 4/2000 | Von Oepen |
| 6,056,767 | A | 5/2000 | Boussignac et al. |
| 6,059,811 | A | 5/2000 | Pinchasik et al. |
| 6,068,656 | A | 5/2000 | Von Oepen |
| 6,071,308 | A | 6/2000 | Ballou et al. |
| 6,086,610 | A | 7/2000 | Duerig et al. |
| 6,099,561 | A | 8/2000 | Alt |
| 6,106,548 | A | 8/2000 | Roubin et al. |
| 6,113,627 | A | 9/2000 | Jang |
| 6,117,165 | A | 9/2000 | Becker |
| 6,117,535 | A | 9/2000 | Szycher et al. |
| 6,132,460 | A | 10/2000 | Thompson |
| 6,136,023 | A | 10/2000 | Boyle |
| 6,152,957 | A | 11/2000 | Jang |
| 6,165,212 | A | 12/2000 | Dereume et al. |
| 6,168,409 | B1 | 1/2001 | Fare |
| 6,174,326 | B1 | 1/2001 | Kitaoka et al. |
| 6,179,868 | B1 | 1/2001 | Burpee et al. |
| 6,190,403 | B1 * | 2/2001 | Fischell et al. ............... 623/1.16 |
| 6,193,744 | B1 | 2/2001 | Ehr et al. |
| 6,193,747 | B1 | 2/2001 | Von Oepen |
| 6,200,334 | B1 | 3/2001 | Jang |
| 6,200,335 | B1 | 3/2001 | Igaki |
| 6,203,569 | B1 | 3/2001 | Wijay |
| 6,231,598 | B1 | 5/2001 | Berry et al. |
| 6,231,600 | B1 | 5/2001 | Zhong |
| 6,241,762 | B1 | 6/2001 | Shanley |
| 6,245,101 | B1 | 6/2001 | Drasler et al. |
| 6,253,443 | B1 | 7/2001 | Johnson |
| 6,258,116 | B1 | 7/2001 | Hojeibane |
| 6,261,318 | B1 | 7/2001 | Lee et al. |
| 6,264,688 | B1 | 7/2001 | Herklotz et al. |
| 6,264,690 | B1 | 7/2001 | Von Oepen |
| 6,270,524 | B1 | 8/2001 | Kim |
| 6,273,913 | B1 | 8/2001 | Wright et al. |
| 6,299,604 | B1 | 10/2001 | Ragheb et al. |
| 6,299,635 | B1 | 10/2001 | Frantzen |
| 6,325,825 | B1 | 12/2001 | Kula et al. |
| 6,331,189 | B1 | 12/2001 | Wolinsky et al. |
| 6,332,089 | B1 | 12/2001 | Acker et al. |

(56) References Cited

U.S. PATENT DOCUMENTS

| | | |
|---|---|---|
| 6,340,366 B2 | 1/2002 | Wijay |
| 6,348,065 B1 | 2/2002 | Brown et al. |
| 6,377,835 B1 | 4/2002 | Schoenberg et al. |
| 6,395,020 B1 | 5/2002 | Ley et al. |
| 6,416,539 B1 | 7/2002 | Hassdenteufel |
| 6,436,132 B1 | 8/2002 | Patel et al. |
| 6,443,982 B1 | 9/2002 | Israel et al. |
| 6,451,049 B2 | 9/2002 | Vallana et al. |
| 6,485,508 B1 | 11/2002 | McGuinness |
| 6,488,702 B1 | 12/2002 | Besselink |
| 6,491,718 B1 | 12/2002 | Ahmad |
| 6,503,272 B2 | 1/2003 | Duerig et al. |
| 6,506,211 B1 | 1/2003 | Skubitz et al. |
| 6,508,834 B1 | 1/2003 | Pinchasik et al. |
| 6,540,776 B2 | 4/2003 | Sanders Millare et al. |
| 6,558,415 B2 | 5/2003 | Thompson |
| 6,562,065 B1 | 5/2003 | Shanley |
| 6,572,646 B1 | 6/2003 | Boylan et al. |
| 6,589,276 B2 | 7/2003 | Pinchasik et al. |
| 6,602,285 B1 | 8/2003 | Von Oepen et al. |
| 6,616,689 B1* | 9/2003 | Ainsworth et al. .......... 623/1.16 |
| 6,624,097 B2 | 9/2003 | Martin et al. |
| D481,139 S | 10/2003 | Seibold et al. |
| 6,629,994 B2* | 10/2003 | Gomez et al. ................. 623/1.15 |
| 6,652,574 B1 | 11/2003 | Jayaraman |
| 6,676,701 B2 | 1/2004 | Rourke et al. |
| 6,679,911 B2 | 1/2004 | Burgermeister |
| 6,682,554 B2* | 1/2004 | Oepen et al. .................. 623/1.15 |
| 6,723,119 B2 | 4/2004 | Pinchasik et al. |
| 6,730,252 B1 | 5/2004 | Teoh et al. |
| 6,740,114 B2 | 5/2004 | Burgermeister |
| 6,749,629 B1 | 6/2004 | Hong et al. |
| 6,755,856 B2 | 6/2004 | Fierens et al. |
| 6,761,733 B2 | 7/2004 | Chobotov et al. |
| 6,770,088 B1 | 8/2004 | Jang |
| 6,776,794 B1 | 8/2004 | Hong et al. |
| 6,786,922 B2 | 9/2004 | Schaeffer |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 | 4/2005 | Pinchasik et al. |
| 6,881,222 B2 | 4/2005 | White et al. |
| 6,896,697 B1* | 5/2005 | Yip et al. ..................... 623/1.15 |
| 6,913,619 B2 | 7/2005 | Brown et al. |
| 6,942,689 B2 | 9/2005 | Majercak |
| 6,955,686 B2 | 10/2005 | Majercak et al. |
| 6,998,060 B2 | 2/2006 | Tomonto |
| 7,029,493 B2 | 4/2006 | Majercak et al. |
| 7,060,093 B2 | 6/2006 | Dang et al. |
| 7,128,756 B2 | 10/2006 | Lowe et al. |
| 7,141,062 B1 | 11/2006 | Pinchasik et al. |
| 7,179,286 B2 | 2/2007 | Lenz |
| 7,204,848 B1 | 4/2007 | Brown et al. |
| 7,329,277 B2 | 2/2008 | Addonizio et al. |
| 7,520,892 B1* | 4/2009 | Ainsworth et al. .......... 623/1.16 |
| 7,611,531 B2 | 11/2009 | Calisse |
| 7,625,398 B2 | 12/2009 | Clifford et al. |
| 7,686,843 B2 | 3/2010 | Moore |
| 7,766,956 B2 | 8/2010 | Jang |
| 2001/0007955 A1 | 7/2001 | Drasler et al. |
| 2001/0027339 A1 | 10/2001 | Boatman et al. |
| 2001/0049549 A1 | 12/2001 | Boylan et al. |
| 2002/0019660 A1 | 2/2002 | Gianotti et al. |
| 2002/0055770 A1 | 5/2002 | Doran et al. |
| 2002/0065549 A1 | 5/2002 | White et al. |
| 2002/0107560 A1 | 8/2002 | Richter |
| 2002/0111669 A1 | 8/2002 | Pazienza et al. |
| 2002/0113331 A1 | 8/2002 | Zhang et al. |
| 2002/0151964 A1 | 10/2002 | Smith et al. |
| 2002/0169499 A1 | 11/2002 | Zilla et al. |
| 2003/0055487 A1 | 3/2003 | Calisse |
| 2003/0083736 A1 | 5/2003 | Brown et al. |
| 2003/0114918 A1 | 6/2003 | Garrison et al. |
| 2003/0120334 A1 | 6/2003 | Gerberding |
| 2004/0002753 A1* | 1/2004 | Burgermeister et al. ..... 623/1.15 |
| 2004/0051201 A1 | 3/2004 | Greenhalgh et al. |
| 2004/0093073 A1 | 5/2004 | Lowe et al. |
| 2004/0102836 A1* | 5/2004 | Fischell et al. ............... 623/1.15 |
| 2004/0126405 A1 | 7/2004 | Sahatjian et al. |
| 2004/0167615 A1 | 8/2004 | Lenz |
| 2004/0193250 A1 | 9/2004 | Von Oepen et al. |
| 2004/0230293 A1 | 11/2004 | Yip et al. |
| 2004/0236407 A1 | 11/2004 | Fierens et al. |
| 2004/0243220 A1 | 12/2004 | Gianotti et al. |
| 2004/0267353 A1* | 12/2004 | Gregorich .................... 623/1.16 |
| 2005/0004650 A1 | 1/2005 | Oepen et al. |
| 2005/0004651 A1 | 1/2005 | Von Oepen et al. |
| 2005/0004658 A1 | 1/2005 | Oepen et al. |
| 2005/0004659 A1 | 1/2005 | Von Oepen et al. |
| 2005/0004662 A1 | 1/2005 | Von Oepen et al. |
| 2005/0043777 A1 | 2/2005 | Von Oepen et al. |
| 2005/0043778 A1 | 2/2005 | Von Oepen et al. |
| 2005/0075716 A1 | 4/2005 | Yan |
| 2005/0222671 A1 | 10/2005 | Schaeffer et al. |
| 2006/0015173 A1 | 1/2006 | Clifford et al. |
| 2006/0106452 A1 | 5/2006 | Niermann |
| 2006/0142844 A1 | 6/2006 | Lowe et al. |
| 2006/0175727 A1 | 8/2006 | Fierens et al. |
| 2006/0184232 A1 | 8/2006 | Gianotti et al. |
| 2006/0206195 A1 | 9/2006 | Calisse |
| 2006/0247759 A1* | 11/2006 | Burpee et al. ................ 623/1.15 |
| 2007/0021827 A1 | 1/2007 | Lowe et al. |
| 2007/0021834 A1 | 1/2007 | Young et al. |
| 2007/0135891 A1 | 6/2007 | Schneider |
| 2007/0179593 A1 | 8/2007 | Fierens et al. |
| 2007/0179601 A1 | 8/2007 | Fierens et al. |
| 2007/0213800 A1 | 9/2007 | Fierens et al. |
| 2007/0299505 A1 | 12/2007 | Gregorich et al. |
| 2008/0077231 A1 | 3/2008 | Heringes et al. |
| 2008/0294239 A1 | 11/2008 | Casey |
| 2008/0294240 A1 | 11/2008 | Casey |
| 2009/0163992 A1 | 6/2009 | Osman et al. |
| 2009/0163997 A1 | 6/2009 | Casey |
| 2009/0163998 A1 | 6/2009 | Casey |
| 2010/0057190 A1* | 3/2010 | Issenmann ................... 623/1.16 |
| 2011/0004289 A1 | 1/2011 | Oepen et al. |
| 2012/0165921 A1 | 6/2012 | Casey |

FOREIGN PATENT DOCUMENTS

| | | |
|---|---|---|
| EP | 0357003 | 3/1990 |
| EP | 0221570 | 1/1991 |
| EP | 565251 | 10/1993 |
| EP | 0699451 | 3/1996 |
| EP | 0709067 | 5/1996 |
| EP | 0808614 | 11/1997 |
| EP | 0815806 | 1/1998 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7-24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO96/21404 | 7/1996 |
| WO | WO96/25124 | 8/1996 |
| WO | WO96/26689 | 9/1996 |
| WO | WO97/12563 | 4/1997 |
| WO | WO97/12564 | 4/1997 |
| WO | WO97/14375 | 4/1997 |
| WO | WO98/32412 | 7/1998 |
| WO | WO98/47447 | 10/1998 |
| WO | WO99/07308 | 2/1999 |
| WO | WO99/17680 | 4/1999 |
| WO | WO99/23976 | 5/1999 |

(56) References Cited

FOREIGN PATENT DOCUMENTS

| WO | WO99/38456 | 8/1999 |
|---|---|---|
| WO | WO99/38458 | 8/1999 |
| WO | WO99/39660 | 8/1999 |
| WO | WO99/39663 | 8/1999 |
| WO | WO99/49928 | 10/1999 |
| WO | WO 00/13611 | 3/2000 |
| WO | WO00/18328 | 4/2000 |
| WO | WO00/32241 | 6/2000 |
| WO | WO00/45744 | 8/2000 |
| WO | WO00/53119 | 9/2000 |
| WO | WO01/01885 | 1/2001 |
| WO | WO01/82835 | 11/2001 |
| WO | WO02/26164 | 4/2002 |
| WO | WO02/064061 | 8/2002 |
| WO | WO02/064065 | 8/2002 |
| WO | WO02/094127 | 11/2002 |
| WO | WO03/009779 | 2/2003 |
| WO | WO03/057076 | 7/2003 |
| WO | WO2004/087015 | 10/2004 |
| WO | WO2006/055533 | 5/2006 |
| WO | WO2006/066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |
| WO | WO2009/080326 | 7/2009 |
| WO | WO2009/080327 | 7/2009 |

OTHER PUBLICATIONS

U.S. Appl. No. 11/731,820, filed Mar. 30, 2011, Issue Notification.
U.S. Appl. No. 12/949,481, filed Nov. 18, 2010, Schneider.
U.S. Appl. No. 12/608,335, filed Oct. 29, 2009, Calisse.
U.S. Appl. No. 10/241,523, Aug. 18, 2004, Office Action.
U.S. Appl. No. 10/241,523, Oct. 25, 2004, Office Action.
U.S. Appl. No. 10/241,523, Mar. 8, 2005, Office Action.
U.S. Appl. No. 10/241,523, Jun. 3, 2005, Office Action.
U.S. Appl. No. 10/241,523, Aug. 23, 2005, Office Action.
U.S. Appl. No. 10/241,523, Nov. 16, 2005, Office Action.
U.S. Appl. No. 10/241,523, Apr. 27, 2006, Office Action.
U.S. Appl. No. 10/743,857, Feb. 12, 2010, Notice of Allowance.
U.S. Appl. No. 10/859,636, Feb. 1, 2010, Notice of Allowance.
U.S. Appl. No. 10/903,013, Feb. 12, 2010, Notice of Allowance.
U.S. Appl. No. 10/903,014, Feb. 5, 2010, Notice of Allowance.
U.S. Appl. No. 10/955,425, Feb. 26, 2010, Notice of Allowance.
U.S. Appl. No. 11/404,450, Apr. 22, 2010, Office Action.
U.S. Appl. No. 11/435,260, Jan. 10, 2008, Office Action.
U.S. Appl. No. 11/435,260, Mar. 26, 2008, Office Action.
U.S. Appl. No. 11/435,260, Dec. 16, 2008, Office Action.
U.S. Appl. No. 11/435,260, Jun. 18, 2009, Notice of Allowance.
U.S. Appl. No. 11/435,260, Jun. 26, 2009, Notice of Allowance.
U.S. Appl. No. 11/731,820, Jan. 27, 2010, Office Action.
U.S. Appl. No. 11/731,882, Feb. 3, 2010, Office Action.
U.S. Appl. No. 11/805,584, Apr. 27, 2009, Office Action.
U.S. Appl. No. 11/805,584, Oct. 29, 2009, Office Action.
U.S. Appl. No. 11/805,584, Mar. 15, 2010, Office Action.
U.S. Appl. No. 11/961,384, May 26, 2009, Office Action.
U.S. Appl. No. 11/961,384, Oct. 8, 2009, Office Action.
U.S. Appl. No. 11/961,754, Jul. 22, 2009, Office Action.
U.S. Appl. No. 11/961,754, Apr. 5, 2010, Notice of Allowance.
U.S. Appl. No. 11/973,707, Jun. 9, 2009, Office Action.
U.S. Appl. No. 11/973,707, Mar. 19, 2010, Office Action.
U.S. Appl. No. 11/961,775, Oct. 1, 2009, Office Action.
U.S. Appl. No. 11/961,775, Mar. 31, 2010, Office Action.
U.S. Appl. No. 12/608,335, May 11, 2012, Office Action.
U.S. Appl. No. 12/966,916, May 23, 2012, Notice of Allowance.
U.S. Appl. No. 60/637,495, filed Dec. 20, 2004, Fierens et al.
U.S. Appl. No. 09/582,318, Aug. 14, 2002, Office Action.
U.S. Appl. No. 09/582,318, Mar. 7, 2003, Notice of Allowance.
U.S. Appl. No. 09/742,144, Sep. 24, 2002, Office Action.
U.S. Appl. No. 09/742,144, May 14, 2003, Office Action.
U.S. Appl. No. 09/742,144, Aug. 29, 2003, Notice of Allowance.
U.S. Appl. No. 09/916,394, Aug. 12, 2003, Office Action.
U.S. Appl. No. 09/916,394, Oct. 9, 2003, Office Action.
U.S. Appl. No. 09/916,394, Mar. 2, 2004, Office Action.
U.S. Appl. No. 09/967,789, Sep. 17, 2003, Office Action.
U.S. Appl. No. 09/967,789, Feb. 17, 2004, Notice of Allowance.
U.S. Appl. No. 10/743,857, Mar. 15, 2007, Office Action.
U.S. Appl. No. 10/743,857, Nov. 16, 2007, Office Action.
U.S. Appl. No. 10/743,857, May 8, 2008, Office Action.
U.S. Appl. No. 10/743,857, Jan. 6, 2009, Office Action.
U.S. Appl. No. 10/743,857, May 27, 2009, Office Action.
U.S. Appl. No. 10/743,857, Jun. 25, 2010, Notice of Allowance.
U.S. Appl. No. 10/859,636, Jun. 1, 2007, Office Action.
U.S. Appl. No. 10/859,636, Dec. 31, 2007, Office Action.
U.S. Appl. No. 10/859,636, Apr. 15, 2008, Office Action.
U.S. Appl. No. 10/859,636, Oct. 1, 2008, Notice of Allowance.
U.S. Appl. No. 10/859,636, Mar. 5, 2009, Office Action.
U.S. Appl. No. 10/859,636, Oct. 19, 2009, Notice of Allowance.
U.S. Appl. No. 10/859,636, May 19, 2010, Notice of Allowance.
U.S. Appl. No. 10/884,613, Mar. 30, 2005, Office Action.
U.S. Appl. No. 10/884,613, Nov. 14, 2005, Office Action.
U.S. Appl. No. 10/903,013, Mar. 15, 2007, Office Action.
U.S. Appl. No. 10/903,013, Nov. 19, 2007, Office Action.
U.S. Appl. No. 10/903,013, May 14, 2008, Office Action.
U.S. Appl. No. 10/903,013, Jan. 5, 2009, Office Action.
U.S. Appl. No. 10/903,013, May 27, 2009, Office Action.
U.S. Appl. No. 10/903,013, Jun. 24, 2010, Notice of Allowance.
U.S. Appl. No. 10/903,014, Mar. 15, 2007, Office Action.
U.S. Appl. No. 10/903,014, Nov. 16, 2007, Office Action.
U.S. Appl. No. 10/903,014, May 13, 2008, Office Action.
U.S. Appl. No. 10/903,014, Jan. 13, 2009, Office Action.
U.S. Appl. No. 10/903,014, Jun. 1, 2009, Office Action.
U.S. Appl. No. 10/903,014, May 26, 2010, Office Action.
U.S. Appl. No. 10/903,014, Jun. 24, 2010, Notice of Allowance.
U.S. Appl. No. 10/903,080, Mar. 15, 2007, Office Action.
U.S. Appl. No. 10/903,080, Nov. 19, 2007, Office Action.
U.S. Appl. No. 10/903,080, May 12, 2008, Office Action.
U.S. Appl. No. 10/903,080, Dec. 30, 2008, Office Action.
U.S. Appl. No. 10/903,080, May 27, 2009, Office Action.
U.S. Appl. No. 10/903,080, Jan. 13, 2010, Notice of Allowance.
U.S. Appl. No. 10/909,117, Aug. 22, 2007, Office Action.
U.S. Appl. No. 10/909,117, May 12, 2008, Office Action.
U.S. Appl. No. 10/909,117, Dec. 30, 2008, Office Action.
U.S. Appl. No. 10/909,117, May 27, 2009, Office Action.
U.S. Appl. No. 10/909,117, Jan. 13, 2010, Notice of Allowance.
U.S. Appl. No. 10/909,118, Mar. 29, 2007, Office Action.
U.S. Appl. No. 10/909,118, Nov. 19, 2007, Office Action.
U.S. Appl. No. 10/909,118, May 12, 2008, Office Action.
U.S. Appl. No. 10/909,118, Jan. 5, 2009, Office Action.
U.S. Appl. No. 10/909,118, Jul. 24, 2009, Office Action.
U.S. Appl. No. 10/909,118, Jan. 13, 2010, Notice of Allowance.
U.S. Appl. No. 10/954,948, Mar. 15, 2007, Office Action.
U.S. Appl. No. 10/954,948, Nov. 16, 2007, Office Action.
U.S. Appl. No. 10/954,948, May 15, 2008, Office Action.
U.S. Appl. No. 10/954,948, Jan. 13, 2009, Office Action.
U.S. Appl. No. 10/954,948, May 29, 2009, Office Action.
U.S. Appl. No. 10/954,948, Jan. 13, 2010, Notice of Allowance.
U.S. Appl. No. 10/954,948, Jul. 6, 2010, Notice of Allowance.
U.S. Appl. No. 10/955,425, Mar. 15, 2007, Office Action.
U.S. Appl. No. 10/955,425, Nov. 16, 2007, Office Action.
U.S. Appl. No. 10/955,425, May 13, 2008, Office Action.
U.S. Appl. No. 10/955,425, Jan. 13, 2009, Office Action.
U.S. Appl. No. 10/955,425, May 28, 2009, Office Action.
U.S. Appl. No. 10/955,425, Jun. 25, 2010, Notice of Allowance.
U.S. Appl. No. 11/313,110, Jan. 8, 2008, Office Action.
U.S. Appl. No. 11/313,110, Jul. 2, 2008, Office Action.
U.S. Appl. No. 11/313,110, Mar. 3, 2009, Office Action.
U.S. Appl. No. 11/313,110, Nov. 2, 2009, Notice of Allowance.
U.S. Appl. No. 11/313,110, Feb. 18, 2010, Notice of Allowance.
U.S. Appl. No. 11/313,110, Jun. 15, 2010, Notice of Allowance.
U.S. Appl. No. 11/404,450, Feb. 4, 2009, Office Action.
U.S. Appl. No. 11/404,450, Mar. 17, 2009, Office Action.
U.S. Appl. No. 11/404,450, Sep. 30, 2009, Office Action.

(56) References Cited

OTHER PUBLICATIONS

U.S. Appl. No. 11/601,475, Jul. 22, 2008, Office Action.
U.S. Appl. No. 11/601,475, Jan. 6, 2009, Office Action.
U.S. Appl. No. 11/601,475, Jun. 1, 2009, Office Action.
U.S. Appl. No. 11/601,475, Jan. 15, 2010, Notice of Allowance.
U.S. Appl. No. 11/601,475, Jul. 9, 2010, Notice of Allowance.
U.S. Appl. No. 11/732,244, Sep. 28, 2009, Office Action.
U.S. Appl. No. 11/732,244, May 5, 2010, Notice of Allowance.
U.S. Appl. No. 11/732,244, Jun. 21, 2010, Notice of Allowance.
U.S. Appl. No. 11/973,707, Oct. 12, 2011, Notice of Allowance.
U.S. Appl. No. 10/909,118, Sep. 21, 2010, Notice of Allowance.
U.S. Appl. No. 11/805,584, Oct. 4, 2010, Office Action.
U.S. Appl. No. 12/895,032, filed Sep. 30, 2010, Fierens et al.
U.S. Appl. No. 10/903,080, Jan. 26, 2011, Issue Notification.
U.S. Appl. No. 11/601,475, Jan. 26, 2011, Issue Notification.
U.S. Appl. No. 12/966,916, Jun. 10, 2011, Office Action.
U.S. Appl. No. 12/895,032, Jul. 3, 2012, Office Action.
U.S. Appl. No. 11/973,707, Feb. 15, 2012, Issue Notification.
U.S. Appl. No. 12/949,481, Feb. 15, 2012, Office Action.
U.S. Appl. No. 11/731,882, Dec. 14, 2011, Issue Notification.
U.S. Appl. No. 12/949,481, Jan. 5, 2012, Office Action.
U.S. Appl. No. 12/966,916, Jan. 5, 2012, Office Action.
U.S. Appl. No. 11/404,450, Jan. 31, 2012, Office Action.
U.S. Appl. No. 12/895,032, Feb. 1, 2012, Office Action.
U.S. Appl. No. 11/805,584, May 12, 2011, Notice of Allowance.
U.S. Appl. No. 13/089,039, filed Apr. 8, 2011, Fierens et al.
U.S. Appl. No. 10/743,857, Aug. 18, 2010, Issue Notification.
U.S. Appl. No. 10/903,013, Aug. 18, 2010, Issue Notification.
U.S. Appl. No. 11/731,820, Aug. 5, 2010, Notice of Allowance.
U.S. Appl. No. 11/961,754, Jul. 28, 2010, Notice of Allowance.
U.S. Appl. No. 11/404,450, Nov. 26, 2010, Office Action.
U.S. Appl. No. 10/859,636, Dec. 9, 2010, Notice of Allowance.
U.S. Appl. No. 11/961,754, Nov. 23, 2010, Issue Notification.
U.S. Appl. No. 12/966,916, filed Dec. 13, 2010, Casey.
U.S. Appl. No. 10/909,117, Nov. 17, 2010, Issue Notification.
U.S. Appl. No. 11/731,820, Dec. 16, 2010, Notice of Allowance.
U.S. Appl. No. 11/404,450, Aug. 10, 2011, Office Action.
U.S. Appl. No. 11/961,384, Apr. 23, 2012, Office Action.
U.S. Appl. No. 12/875,971, Apr. 19, 2012, Office Action.
U.S. Appl. No. 11/731,882, Aug. 29, 2011, Notice of Allowance.
U.S. Appl. No. 11/805,584, Aug. 24, 2011, Issue Notification.
U.S. Appl. No. 10/903,014, Aug. 25, 2010, Issue Notification.
U.S. Appl. No. 10/903,080, Sep. 16, 2010, Notice of Allowance.
U.S. Appl. No. 10/909,117, Sep. 16, 2010, Notice of Allowance.
U.S. Appl. No. 10/955,425, Sep. 30, 2010, Notice of Allowance.
U.S. Appl. No. 11/313,110, Sep. 29, 2010, Issue Notification.
U.S. Appl. No. 11/731,882, Sep. 1, 2010, Office Action.
U.S. Appl. No. 11/732,244, Sep. 22, 2010, Issue Notification.
Landers, Rüdiger and Mülhaupt, Rolf "Desktop manufacturing of complex objects, prototypes and biomedical scaffolds by means of computer-assisted design combined with computer-guided 3D plotting of polymers and reactive oligomers" Macromolecular Materials and Engineering, vol. 282, Issue 1, pp. 17-21, Oct. 2000.
U.S. Appl. No. 11/961,384, Aug. 21, 2012, Notice of Allowance.
U.S. Appl. No. 12/875,971, Jul. 26, 2012, Notice of Allowance.
U.S. Appl. No. 12/875,971, Oct. 17, 2012, Issue Notification.
U.S. Appl. No. 12/949,481, Aug. 13, 2012, Notice of Allowance.
U.S. Appl. No. 13/089,039, Oct. 16, 2012, Office Action.
U.S. Appl. No. 13/411,135, Oct. 16, 2012, Restriction Requirement.
U.S. Appl. No. 12/895,032, Aug. 13, 2013, Office Action.
U.S. Appl. No. 13/089,039, Jun. 28, 2013, Office Action.
U.S. Appl. No. 13/411,135, Mar. 15, 2013, Office Action.
U.S. Appl. No. 13/801,469, filed Mar. 13, 2013, Von Oepen et al.
U.S. Appl. No. 12/608,335, Dec. 2, 2013, Office Action.
U.S. Appl. No. 12/608,335, Mar. 3, 2014, Advisory Action.
U.S. Appl. No. 12/895,032, Oct. 29, 2013, Office Action.
U.S. Appl. No. 12/895,032, Mar. 14, 2014, Office Action.
U.S. Appl. No. 13/089,039, Sep. 26, 2013, Office Action.
U.S. Appl. No. 13/089,039, Apr. 14, 2014, Notice of Allowance.
U.S. Appl. No. 13/089,039, Aug. 6, 2014, Issue Notification.
U.S. Appl. No. 13/411,135, Oct. 8, 2013, Office Action.
U.S. Appl. No. 13/411,135, Mar. 14, 2014, Office Action.
U.S. Appl. No. 14/323,658, filed Jul. 3, 2014, Fierens et al.
U.S. Appl. No. 13/411,135, Oct. 24, 2014, Office Action.

* cited by examiner

ENDOPROSTHESIS HAVING A STABLE ARCHITECTURE

FIELD OF THE INVENTION

The present invention relates to an endoprosthesis having elevated scaffolding properties and also elevated flexibility. More particularly, the present invention relates to an endoprosthesis having a plurality of web rings coupled by connectors that are composed of three or more struts of essentially equal length, which extend circumferentially in essentially parallel directions.

BACKGROUND OF THE INVENTION

Applications of endoprotheses to the superior femoral artery (SFA) and to the popliteal artery (PA) has received increased attention because of the prevalence of peripheral arterial disease (PAD) among older patients and because no known endoprosthesis can adequately supports the SFA and the PA without distorting its architecture during patient motion.

PAD is estimated to affect between 3% and 10% of individuals till the age of 70 and may approach 20% of individuals older than 70 years of age. PAD has been associated with an increased risk of coronary artery disease, cerebrovascular disease, and premature death. Moreover, as a consequence of limited exercise performance and walking ability, individuals who have symptoms of intermittent claudication experience a significantly negative impact on quality of life.

Exercise programs have been recommended as the first line of therapy for PAD. Pharmacotherapy with cilostazol provides additional symptom relief, but patients who fail medical therapy and continue to have resting leg pain or non-healing ulcers eventually become candidates for invasive treatment strategy. Unfortunately, surgical revascularization has associated with higher periprocedural morbidity and mortality, making the surgical option less desirable in elderly patients—a significant proportion of patients with PAD.

Because greater than 50% of individuals with lower extremity claudication have atherosclerotic disease confined to the superficial femoral artery (SFA), endovascular techniques have recently emerged to treat this arterial segment.

Stents, grafts and a variety of other endoprostheses are well known and used in endovascular procedures, such as for treating aneurysms, lining or repairing vessel walls, filtering or controlling fluid flow, and expanding or scaffolding occluded or collapsed vessels. Such endoprostheses can be delivered and used in virtually any accessible body lumen of a human or animal and can be deployed by any of a variety of recognized means.

An endoprosthesis is typically delivered by a catheter system to a desired location or deployment site inside a body lumen of a vessel or other tubular organ. To facilitate such delivery, the endoprosthesis must be capable of having a particularly small cross profile and a sufficient degree of longitudinal flexibility during delivery to allow advancement through the anatomy to the deployed site.

Once deployed, the endoprosthesis should be capable of satisfying a variety of performance characteristics. The endoprosthesis should have sufficient rigidity or outer bias to perform its intended function, such as opening a lumen or supporting a vessel wall. Similarly, the endoprosthesis should retain sufficient flexibility along its length in its expanded condition so that it will not kink, straighten or fracture during or after deployment in a curved vessel. The endoprosthesis should also provide a substantially uniform or otherwise controlled scaffolding of the vessel wall and prevent plaque from protruding into the artery.

One type of endoprosthesis is the stent, which is used for the treatment of atherosclerotic stenosis in blood vessels. After a patient undergoes a percutaneous transluminal angioplasty or similar interventional procedure, a stent may be deployed at the treatment site to maintain patency of the vessel. The stent is configured to scaffold or support the treated blood vessel and may be loaded with a beneficial agent, acting as a delivery platform to reduce restenosis or the like.

Numerous endoprosthesis designs and constructions have been developed to address one or more of the performance characteristics summarized above. For example, a variety of stent designs are disclosed in the following patents: U.S. Pat. No. 4,580,568 to Gianturco; U.S. Pat. No. 5,102,417 to Palmaz; U.S. Pat. No. 5,104,404 to Wolff; U.S. Pat. No. 5,133,732 to Wiktor; U.S. Pat. No. 5,292,331 to Boneau; U.S. Pat. No. 5,514,154 to Lau et al.; U.S. Pat. No. 5,569,295 to Lam; U.S. Pat. No. 5,707,386 to Schnepp-Pesch et al.; U.S. Pat. No. 5,733,303 to Israel et al.; U.S. Pat. No. 5,755,771 to Penn et al.; U.S. Pat. No. 5,776,161 to Globerman; U.S. Pat. No. 5,895,406 to Gray et al.; U.S. Pat. No. 6,033,434 to Borghi; U.S. Pat. No. 6,099,561 to Alt; U.S. Pat. No. 6,106,548 to Roubin et al.; U.S. Pat. No. 6,113,627 to Jang; U.S. Pat. No. 6,132,460 to Thompson; U.S. Pat. No. 6,331,189 to Wolinsky; and U.S. Pat. No. 7,128,756 to Lowe et al., the entireties of which are incorporated herein by reference.

During the treatment of some types of SFA and PA disease, relatively long stent lengths are frequently required, at times causing the treating physician to overlap multiple stents. Further complicating the treatment of SFA and PA disease is the possibility of stent fractures and subsequent restenosis. A particular area of vulnerability is the area through the adductor canal as the SFA continues behind the knee; in fact, the area at the adductor canal is a frequent location for SFA disease likely secondary to the bending, compression, elongation and torsion forces on the artery itself due to the muscular structure surrounding this canal, leading to a lengthening and shortening of up to 15% of the stent between straight and bent positions of a limb. After the stent has been implanted, the body vessel is subjected to repeated traumas caused by the negative interaction of a relatively rigid stent and a softer artery.

In the earlier days of endovascular therapy, it was believed that the area to avoid stenting due to the risk of stent crush or stent fracture was near the bony articulation between the femur and the tibia. It is now believed that the area of critical importance is really superior to this point leading up to the adductor canal, which is a frequent location of SFA lesions. If it is necessary to stent this region, the ability of the stent to withstand the forces present in the SFA is of critical importance. Another risk is the incidence of restenosis, against which self-expanding Nitinol stents have shown better one-year patency rates than other types of stents.

Therefore, it would be desirable for the endoprosthesis to provide an elevated degree of scaffolding to a vessel wall while retaining an elevated degree of flexibility within the operating environments of the SFA and PA.

SUMMARY OF THE INVENTION

The present invention relates to an endoprosthesis for delivery within a body lumen that provides an elevated degree of scaffolding and that has an elevated degree of flexibility, making it particularly suited for implantation in body vessels in which extensive bending, compression, elongation, and torsion forces are applied to the endoprosthesis. In different embodiments, the endoprosthesis may be configured as a stent, graft, valve, occlusive device, trocar or aneurysm treatment device for a variety of intralumenal applications, including vascular, coronary, biliary, esophageal, renal, urological and gastrointestinal, for example, for the treatment of SFA and PA diseases.

An endoprosthesis constructed according to the principles of the present invention includes a web structure that is expandable from a contracted configuration to an expanded configuration and that includes a plurality of longitudinally adjacent web rings. Each of the web rings is defined by web elements disposed circumferentially around a longitudinal axis, which are adjoined one to the other at junction bends. A first junction bend in a first web ring is coupled to a second junction bend in a second web ring by a connector that includes three or more struts (for example, five struts) of essentially equal length that extend circumferentially in essentially parallel directions. The struts of the connector are adjoined in sequence by coupling segments that, in one embodiment of the invention, are arcuate in shape.

The connector of the present invention may also include two struts of reduced length, one coupled to the first junction bend and the other one coupled to the second junction bend. To increase density of the endoprosthesis, the coupling segments of one connector may be nested among the coupling segments of another connector adjacent in a circumferential direction.

In different embodiments, the connector may couple a midpoint in the first junction bend to a midpoint in the second junction bend, or may couple an endpoint in the first junction bend to an endpoint in the second junction bend. The first junction bend may be laterally offset in relation to the second junction bend, providing the endoprosthesis with greater ability to absorb torsional stresses.

The connector may span circumferentially for a distance substantially equal to the circumferential spacing between the midpoints of four junction bends, and the interstices between the struts may be narrower than the widths of the struts.

In different embodiments, the endoprosthesis may be a stent, and the struts of the connector may be substantially rectilinear in shape. The web elements may also be substantially rectilinear in shape, or may be shaped like crowns that include a central member disposed essentially parallel to the longitudinal axis of the endoprosthesis in the contracted configuration and connected at its ends to end members that extend at obtuse angles from the central member. In the contracted delivery configuration of the endoprosthesis, the web elements of each web ring are nested one into the other and may be oriented at approximately 180 degrees in relation to the web elements in a neighboring web ring.

The web structure may be manufactured from a shape-memory material and may be configured to self-expand from the contracted configuration to the expanded configuration, or may be expanded by application of a radial pressure to an interior surface of the essentially tubular body, for example, by inflating a balloon disposed inside the endoprosthesis.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to use the present invention in virtually any detailed system, structure or manner.

The present invention relates to an endoprosthesis for delivery within a body lumen that provides an elevated degree of scaffolding and that has an elevated degree of flexibility, making it particularly suited for implantation in body vessels in which extensive bending, compression, elongation, and torsion forces are applied to the endoprosthesis. In different embodiments, the endoprosthesis may be configured as a stent, graft, valve, occlusive device, trocar or aneurysm treatment device for a variety of intralumenal applications, including vascular, coronary, biliary, esophageal, renal, urological and gastrointestinal, for example, for the treatment of SFA and PA diseases.

An endoprosthesis constructed according to the principles of the present invention includes a web structure that is expandable from a contracted delivery configuration to an expanded deployed configuration and that is formed by a plurality of longitudinally adjacent web rings, coupled by connectors that include three or more struts of essentially equal length. The connector struts are joined in sequence and extend circumferentially in essentially parallel directions. For ease of description and without restrictive intent, an embodiment of the invention will be described hereinafter with reference to a stent.

Figure 1:
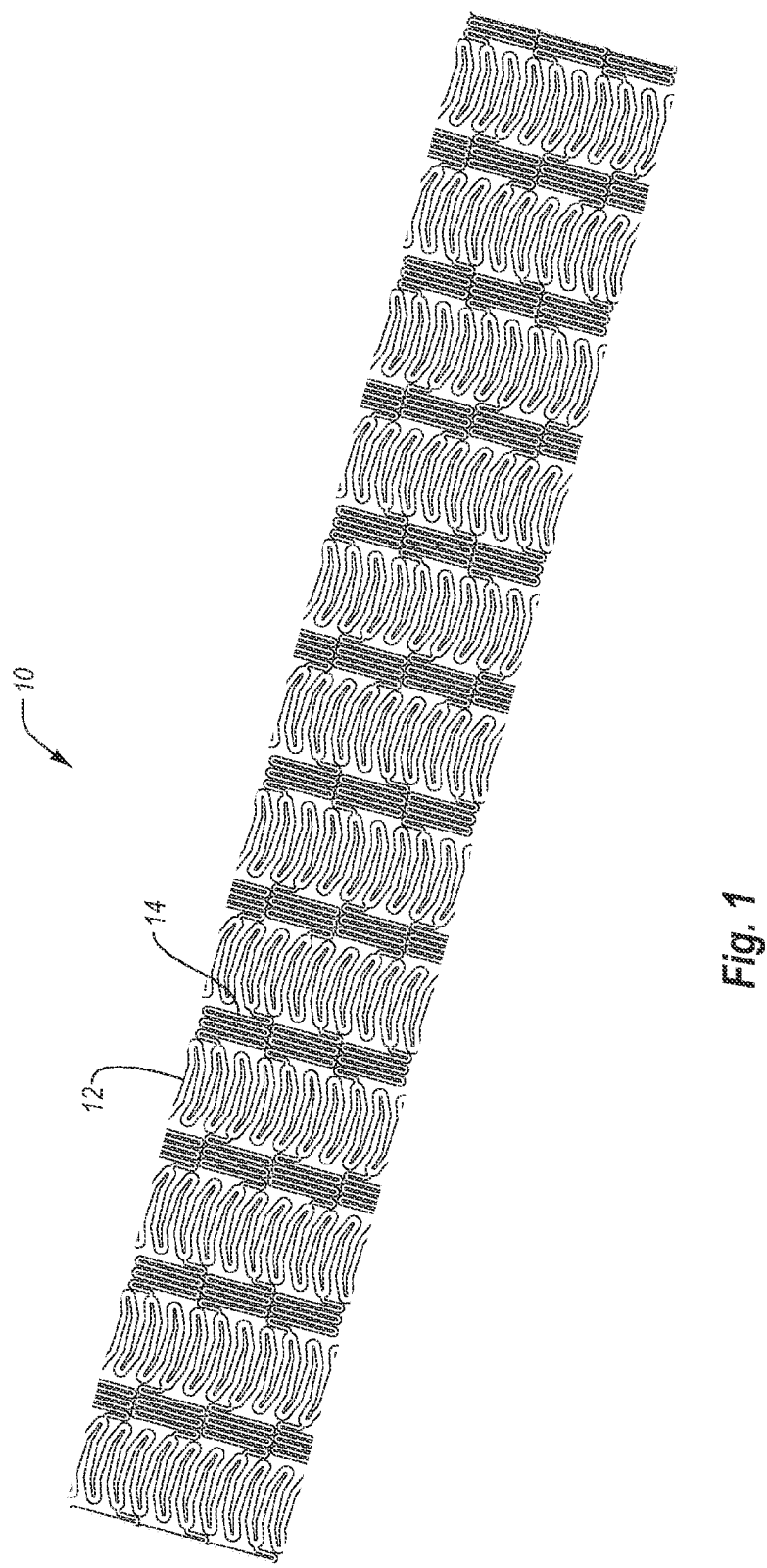
FIG. 1 is a top view of the web structure of a first endoprosthesis, illustrated in a flattened state, according to an embodiment of the invention.

Referring first to FIG. 1, a first embodiment of the invention relates to a stent 10, which is formed by a plurality of web rings 12 that are disposed longitudinally one next to the other and that are adjoined by connectors 14 constructed as described in greater detail hereinbelow. Although the structure of stent 10 is shown in FIG. 1 in flattened form, a person skilled in the art will appreciate that stent 10 is manufactured for clinical use as an essentially tubular body that may have a variety of shapes, for example, a cylindrical, frustoconical, or hyperboloid shape.

Stent 10 may be produced from a variety of biocompatible materials and may be deployed at a target vessel using techniques also known in the art. For example, stent 10 may be manufactured from a shape memory material such as Nitinol (a nickel-titanium alloy) when stent 10 is structured to self-expand after delivery into the target vessel, or may be manufactured from a plastic or metal material such as stainless steel or cobalt chromium alloys when stent 10 is structured to be expanded by inflating a catheter-mounted balloon on which stent 10 is crimped.

Figure 2:
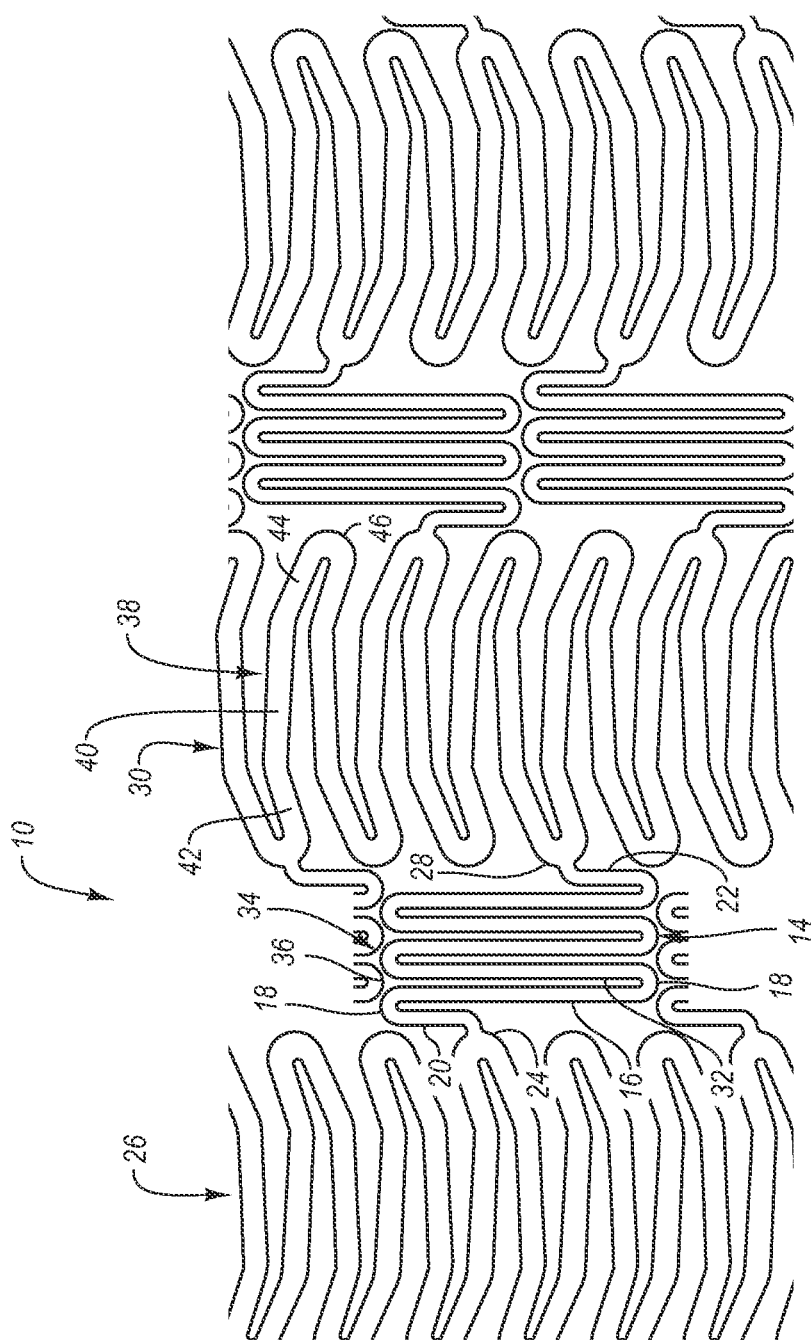
FIG. 2 is a detail view of the web structure of FIG. 1.

Referring now to FIG. 2, connector 14 includes a plurality of struts 16 that extend circumferentially along the surface of stent 10 in essentially parallel directions. In the illustrated embodiment, five struts 16 of equal length are disposed in circumferential directions and are adjoined sequentially by coupling segments 18, but a higher or lower number of struts 16 (e.g. 2, 3, 4, 6, or 7) and coupling segments 18 (e.g. 3, 4, 5, 7, or 8) may be employed, depending on the distances between the web rings and on the desired density (i.e., on the desired amount of material per surface units) of connector 16.

Coupling segments 18 are shown in FIG. 2 as being arcuate, which is a preferred embodiment of the invention because of the optimal stress distribution of stress in rounded segments in comparison with other segment designs. It should be understood, however, that coupling segments 18 may have a variety of other shapes and that shapes that do not contain points of stress concentration are preferred because the risk of stent rupture is reduced with this type of design.

Connector 14 also includes two struts 20 and 22 of reduced length, which are disposed at opposite ends of connector 14 and which couple connector 14 to neighboring web rings 26 and 30. More particularly, strut 20 joins connector 14 to a first junction bend 24 in first web ring 26 and strut 22 joins connector 14 to a second junction bend 28 in second web ring 30.

First junction bend 24 and second junction bend 28 are shown in FIG. 2 as laterally offset one from the other, that is, not aligned longitudinally. This offset arrangement is preferable over arrangements in which first and second junction bends are longitudinally aligned, because this offset arrangement provides for an improved resistance to foreshortening during stent deployment and as a consequence of bending, compression, elongation and torsion stresses applied to stent 10 after implantation.

While FIG. 2 shows that struts 20 and 22 are coupled to the mid-points of junction bends 24 and 28, in other embodiments of the invention struts 20 and 22 may be coupled to other points of junction bends 24 and 28, for example, struts 20 and 22 may be coupled to (or near) the end points of junction bends 24 and 28, in order to maximize the offset distance between junction bends 24 and 28.

In different embodiments, struts 16 may have different lengths. For example, in the embodiment illustrated in FIG. 2, struts 16 are shown as having the same length as the distance between four junction bends in web ring 26 or 30. In other embodiments of the invention, struts 16 may have a variety of other lengths. Further, FIG. 2 shows struts 16 as essentially rectilinear in shape, but in other embodiments of the invention struts 16 may be each formed by a plurality of segments coupled at different angles (in a fashion similar to the web elements defining web rings 26 and 30) or may even have a curved shape.

In different embodiments, struts 16 may also have a variety of different widths. For example, in the embodiment illustrated in FIG. 2, struts 16 are shown as having widths larger than interstices 32 between struts 16, which provides stent 10 with a high degree of surface density and, accordingly, with elevated scaffolding properties.

A plurality of connectors are aligned circumferentially to couple first web ring 26 to second web ring 30 and the distances between two circumferentially adjacent connectors may vary in different embodiments of the invention. In the embodiment illustrated in FIG. 2, connector 14 is disposed as closely as possible to circumferentially adjacent connector 34, such that coupling segments 36 of connector 34 are nested among coupling segments 18 of connector 14.

The web elements of stent 10 may be shaped as crowns 38 adjoined sequentially by junction bends, as illustrated in FIG. 2. More particularly, each of the web elements or crowns 38 depicted in FIG. 2 is formed by a central member 40, disposed essentially parallel to the longitudinal axis of stent 10 in the contracted configuration of stent 10, and by a first and a second end members 42 and 44 that extend from opposite ends of central member 40 at two obtuse angles, which may be the same or different.

In the contracted delivery configuration, crown 38 are nested one into the other. Further, the crowns of neighboring web rings may be disposed in opposite directions, for example, as shown in FIG. 2, the crowns of first web ring 36 may be disposed at 180 degrees in relation to the crowns of second web ring 30. Stents having web elements shaped like the crowns shown in FIG. 2 are described in U.S. Patent Application Publication Nos. 2004/0193250, 2005/0004651, U.S. Pat. Nos. 6,682,554 and 6,602,285, International Publication No. WO 00/13611, and German Patent Publication No. 19840645, the entireties of which are incorporated herein by reference.

A person skilled in the art will appreciate that web elements of still different shapes may be employed in constructing the web rings and that such alternative designs all fall within the spirit and scope of the present invention. For example, the web elements of web rings 26 and 30 may be shaped like essentially rectilinear struts joined one to the other by arcuate junction bends.

Figure 3:
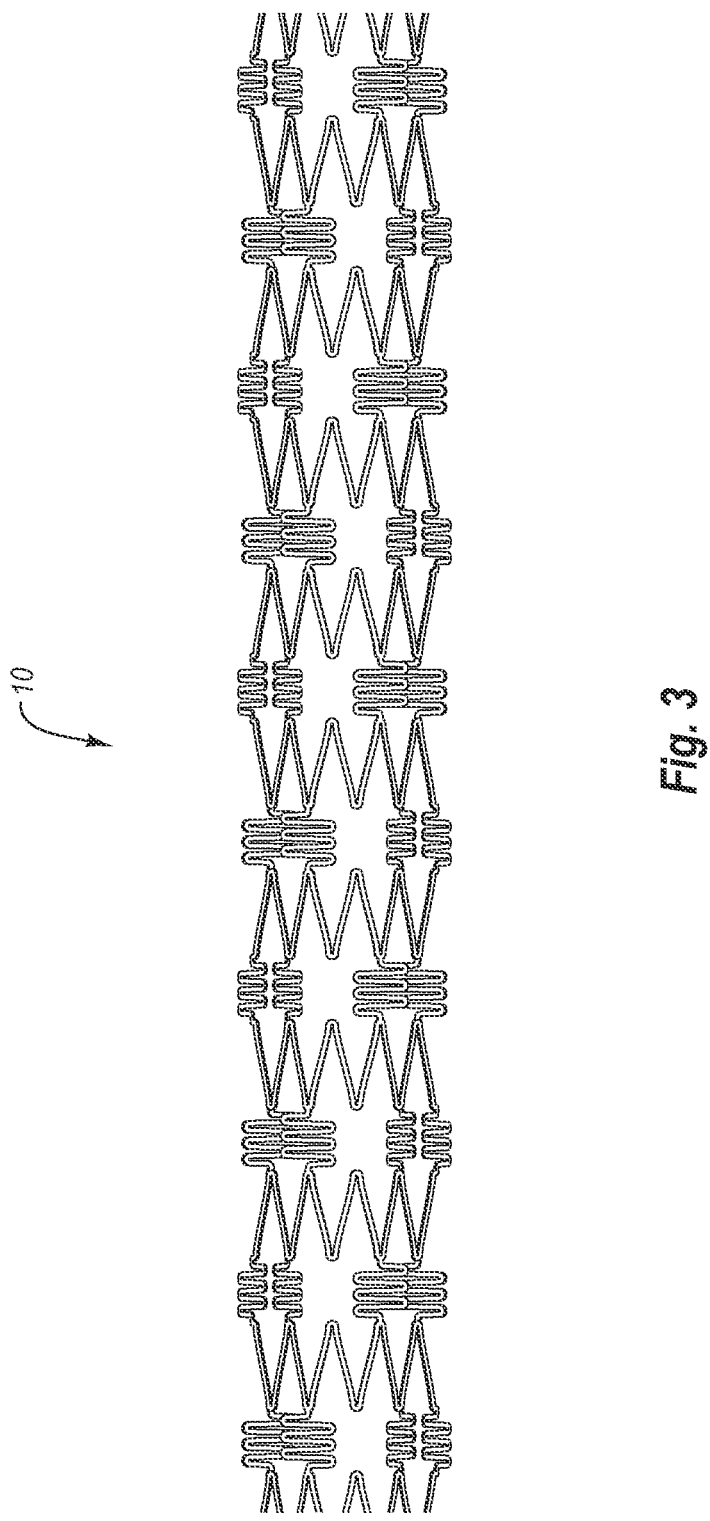
FIG. 3 illustrates an endoprosthesis according to an embodiment of the invention in an at rest state.

The architecture of stent 10 is particularly stable, as can be seen from the photographs enclosed herein as FIGS. 3-6. Referring first to FIG. 3, stent 10 is shown in an at-rest position, without any loads applied thereon. Therefore, FIG. 3 depicts illustrates stent 10 in the configuration described in detail hereinabove, except that FIGS. 1-2 depict stent 10 in a flattened configuration while FIG. 3 reproduces stent 10 in a cylindrical, operative configuration.

Figure 4:
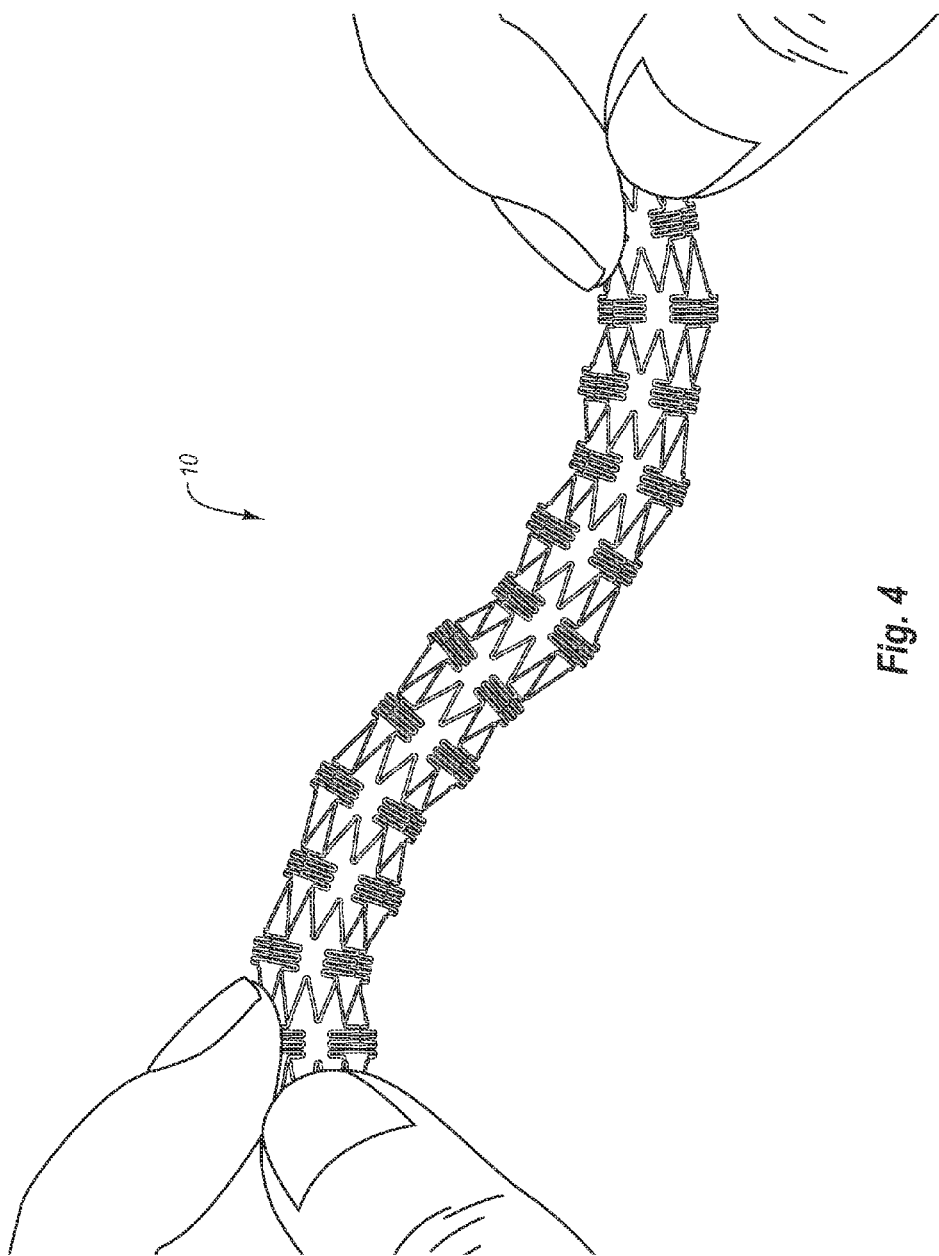
FIG. 4 illustrates the endoprosthesis of FIG. 3 in a bent state.

FIG. 4 depicts stent 10 in a bent configuration. It can be seen that stent 10 still retains its tubular configuration after bending because of the stretching of the connectors (either longitudinally or in fan-like fashion) in the areas of stent 10 under tension, and of the compressing of the connectors (also either longitudinally or in fan-like fashion) in the areas of stent 10 under compression.

Figure 5:
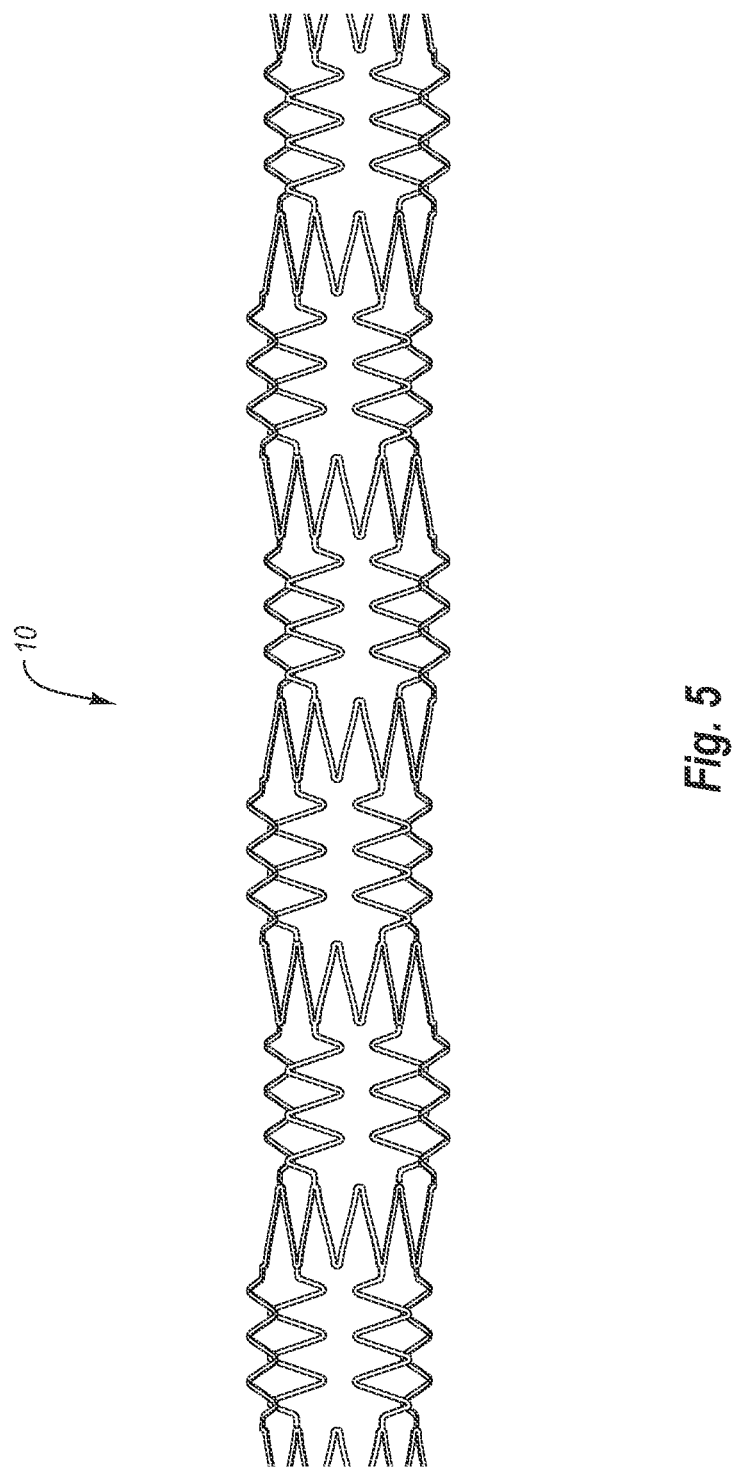
FIG. 5 illustrates the endoprosthesis of FIG. 3 in an elongated state.

FIG. 5 depicts stent 10 in an elongated mode, as a result of tensile forces applied to the longitudinal ends of stent 10. The stable architecture of stent 10 can be seen again, because stent 10 continues to maintain its tubular structure under the applied load.

Figure 6:
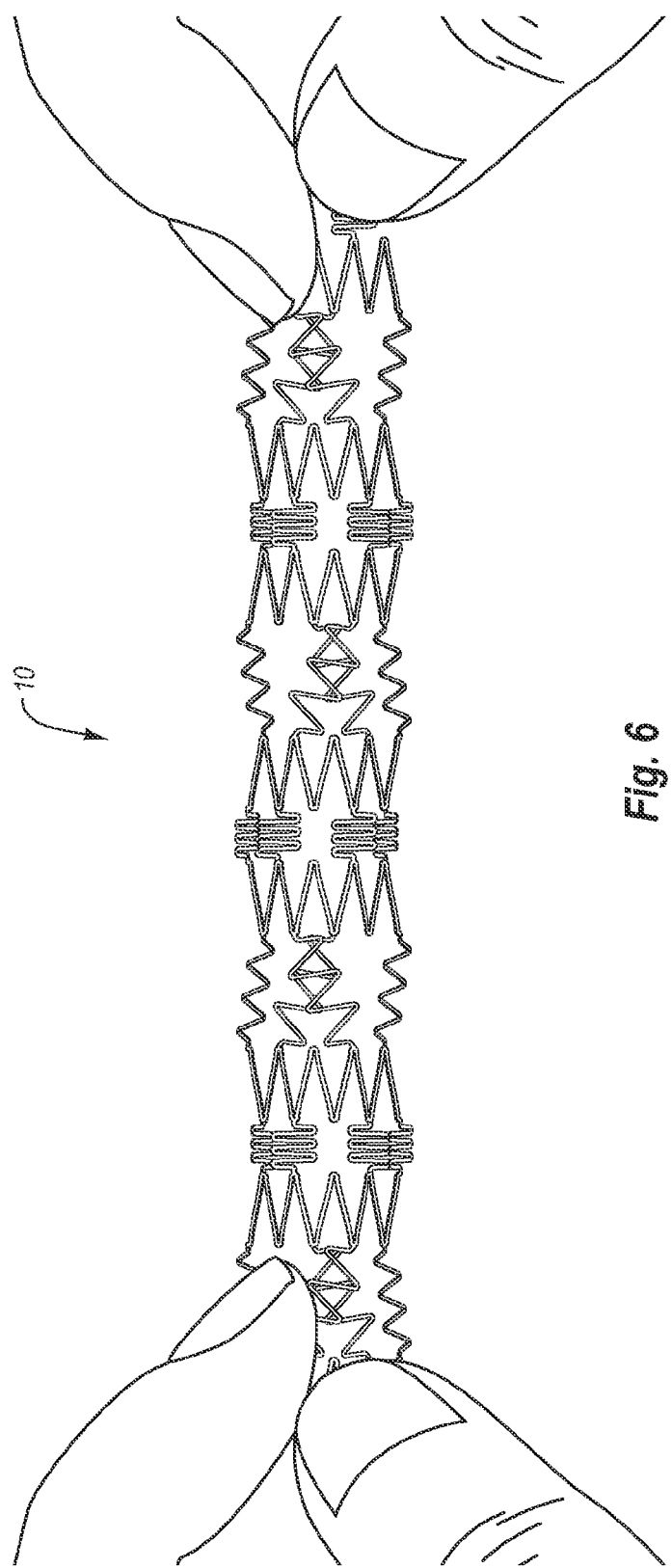
FIG. 6 illustrates the endoprosthesis of FIG. 3 in a twisted state.

FIG. 6 depicts stent 10 when a torsion force applied to its longitudinal ends. As it can be seen, the construction of stent 10 with connectors configured as described hereinabove and coupled to junction bends that are laterally offset from each other causes the connectors to absorb part or all of the torsional stress transmitted between neighboring web rings, which would otherwise cause the neighboring web rings to rotate one in relation to the other and stent 10 to become deformed, possibly leading to the ultimate fracture of stent 10.

Therefore, an endoprosthesis constructed according to the principles of the present invention will have a stable architecture, preventing traumas to the vessel and to the stent and reducing fractures of the endoprosthesis during service.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. An endoprosthesis for delivery in a body lumen comprising:
a tubular body having a longitudinal axis, and having proximal and distal ends and a lumen extending longitudinally therebetween, and a wall having areas thereof removed to define a web structure configured for circumferential expansion from a contracted delivery configuration to an expanded deployed configuration;
the web structure comprising a plurality of longitudinally adjacent web rings interconnected one with another at a plurality of connectors, and that are arranged so that the plurality of web rings are situated side-by-side along the longitudinal length of the tubular body, with each web ring extending circumferentially around the wall, and each web ring comprising web elements joined in pairs at junction bends, each web ring joined in pairs by the plurality of connectors at at least some of the junction bends, the web elements in each web ring are foldable on top of one another and nested one into the other in the contracted delivery configuration, each of the web elements comprising a central member having first and second ends, the central member being disposed parallel to the longitudinal axis in the contracted delivery configuration, the central member being connected at the first end to a first end member at a first obtuse angle, the central member being connected at the second end to a second end member at a second obtuse angle, wherein adjacent web rings comprise a proximal web ring and a distal web ring, the web elements in the proximal web ring being oriented at 180 degrees in relation to the web elements in the distal web ring;
wherein each connector is coupled to a mid-point of its respective junction bends, and each connector is disposed between opposing junction bends of a pair of web rings situated side-by-side, with the opposing junction bends of each web ring facing one another, such that each connector is disposed between the pair of web rings and is longitudinally offset from the pair of web rings, and each connector comprising a plurality of parallel struts joined at arcuate coupling segments so that the parallel struts can be expanded and contracted relative to one another when the stent is stretched or compressed when deployed, the plurality of parallel struts extending circumferentially around at least a portion of the wall a distance that is equal to the spacing between four circumferentially adjacent junction bends on each side of the connector, and each connector being joined on one side to a first pair of web elements of a first web ring at a first junction bend, and joined on its opposite side to a second pair of web elements of an adjacent web ring at a second junction bend, the second pair of web elements being laterally offset from the first pair of web elements;
wherein arcuate coupling segments of a first connector are nested between arcuate coupling segments of a second circumferentially adjacent connector.

2. The endoprosthesis of claim 1, the connector comprising at least five struts of equal length.

3. The endoprosthesis of claim 1, the connector further comprising two struts of reduced length, and one of the struts of reduced length being coupled to the first junction bend and the other strut of reduced length being coupled to the second junction bend.

4. The endoprosthesis of claim 1, the plurality of parallel struts comprising one or more pairs of adjacent parallel struts, the plurality of parallel struts defining interstices between each pair of adjacent parallel struts, the interstices having a longitudinal width that is smaller than a combined longitudinal width of one of the pairs of adjacent parallel struts.

5. The endoprosthesis of claim 1, the connector coupling an endpoint in the first junction bend to an endpoint in the second junction bend.

6. The endoprosthesis of claim 1, the endoprosthesis being a stent.

7. The endoprosthesis of claim 1, the struts being rectilinear in shape.

8. The endoprosthesis of claim 1, the web elements being rectilinear in shape.

9. The endoprosthesis of claim 1, the web structure being configured to self-expand from the contracted delivery configuration to the expanded deployed configuration.

10. The endoprosthesis of claim 1, the web structure being configured to expand from the contracted delivery configuration to the expanded deployed configuration by application of a radial pressure to an interior surface of the tubular body.

11. The endoprosthesis of claim 1, the first and the second obtuse angles being equal.

12. The endoprosthesis of claim 1, the junction bends having an arcuate shape.

13. An endoprosthesis for delivery in a body lumen comprising:
a tubular body having a longitudinal axis, and having proximal and distal ends and a lumen extending longitudinally therebetween, and a wall having areas thereof removed to define a web structure configured for circumferential expansion from a contracted delivery configuration to an expanded deployed configuration;
the web structure comprising a plurality of longitudinally adjacent web rings interconnected one with another at a plurality of serpentine connectors, and that are arranged so that the plurality of web rings are situated side-by-side along the longitudinal length of the tubular body, with each web ring extending circumferentially around the wall, and each web ring comprising web elements joined in pairs at junction bends, each web ring joined in pairs by the plurality of serpentine connectors at at least some of the junction bends, the web elements in each web ring are foldable on top of one another and nested into the other in the contracted delivery configuration, each of the web elements comprising a central member having first and second ends, the central member being disposed parallel to the longitudinal axis in the contracted delivery configuration, the central member being connected at the first end to a first end member at a first obtuse angle, the central member being connected at the second end to a second end member at a second obtuse angle, wherein adjacent web rings comprise a proximal web ring and a distal web ring, the web elements in the proximal web ring being oriented at 180 degrees in relation to the web elements in the distal web ring;
wherein each serpentine connector is coupled to a mid-point of its respective junction bends, and each connector is disposed between opposing junction bends of a pair of web rings situated side-by-side, with the opposing junction bends of each web ring facing one another, such that each serpentine connector is disposed between the pair of web rings and is longitudinally offset from the pair of web rings, and each serpentine connector comprising a plurality of parallel struts joined at arcuate coupling segments so that the parallel struts can be expanded and contracted relative to one another when the stent is stretched or compressed when deployed, the plurality of parallel struts extending circumferentially around at least a portion of the wall a distance that is equal to the spacing between four circumferentially adjacent junction bends on each side of the serpentine connector, and each serpentine connector being joined on one side to a first pair of web elements of a first web ring at a first junction bend, and joined on its opposite side to a second pair of web elements of an adjacent web ring at a second junction bend, and the second pair of web elements being laterally offset from the first pair of web elements, wherein arcuate coupling segments of a first serpentine connector are nested between arcuate coupling segments of a second circumferentially adjacent serpentine connector.

* * * * *